United States Patent
Zheng et al.

(10) Patent No.: US 9,867,219 B1
(45) Date of Patent: Jan. 9, 2018

(54) WIRELESS COMMUNICATION SYSTEM OF SMART CYCLING EQUIPMENT AND METHOD USING SAME

(71) Applicant: Shenzhen Qianhai LIVALL IoT Technology Co., Ltd., Shenzhen, Guangdong Province (CN)

(72) Inventors: Bo Zheng, Shenzhen (CN); Yong-Zheng Ye, Shenzhen (CN); Kai Yu, Shenzhen (CN); Yong Lin, Shenzhen (CN)

(73) Assignee: SHENZHEN QIANHAI LIVALL IOT TECHNOLOGY CO., LTD., Shenzhen, Guangdong Province (CN)

( * ) Notice: Subject to any disclaimer, the term of this patent is extended or adjusted under 35 U.S.C. 154(b) by 0 days.

(21) Appl. No.: 15/371,200

(22) Filed: Dec. 6, 2016

(30) Foreign Application Priority Data

Sep. 30, 2016 (CN) .......................... 2016 1 0873417

(51) Int. Cl.
| | |
|---|---|
| *H04B 7/00* | (2006.01) |
| *H04W 76/02* | (2009.01) |
| *H04W 4/00* | (2009.01) |
| *A61B 5/024* | (2006.01) |
| *A61B 5/00* | (2006.01) |
| *H04W 88/02* | (2009.01) |

(52) U.S. Cl.
CPC ........... *H04W 76/02* (2013.01); *A61B 5/0024* (2013.01); *A61B 5/02438* (2013.01); *H04W 4/008* (2013.01); *H04W 88/02* (2013.01)

(58) Field of Classification Search
CPC ........... B60C 23/0462; B60C 23/0415; B60C 23/0418; B60C 23/0433; B60C 23/0435; B60C 23/0437; B60C 23/0444; B60C 23/0479; B60C 23/0481; B60C 23/0483; H04L 67/12; H04L 1/0061; H04L 2012/40286; H04L 69/18; H04W 24/00; H04W 48/16; H04W 4/008; H04W 88/04; H04W 88/06; H04W 8/005
See application file for complete search history.

(56) References Cited

U.S. PATENT DOCUMENTS

| | | | |
|---|---|---|---|
| 9,167,086 B1* | 10/2015 | Gilor | H04M 3/42221 |
| 2011/0188392 A1* | 8/2011 | Misumi | B63H 21/22 |
| | | | 370/252 |
| 2012/0185110 A1* | 7/2012 | Deniau | B60C 23/0418 |
| | | | 701/1 |
| 2014/0254422 A1* | 9/2014 | Mehta | H04W 8/005 |
| | | | 370/254 |
| 2016/0286891 A1* | 10/2016 | Stramacchia | A42B 3/30 |
| 2016/0335880 A1* | 11/2016 | Treccani | G08B 21/0297 |

* cited by examiner

*Primary Examiner* — Golam Sorowar
(74) *Attorney, Agent, or Firm* — Cheng-Ju Chiang

(57) ABSTRACT

A wireless communication system includes a number of peripheral devices, a wireless communication device, and a terminal. The wireless communication device includes a first communication module and a second communication module. The second communication module includes a host unit and a device unit. The host unit is used to be wirelessly connected to the peripheral devices. The terminal supports the first communication protocol is used to connect to the first communication module, and the terminal supports the second communication protocol is used to connect to the second communication module via the device unit thereof. A method using the wireless communication system is also provided.

4 Claims, 5 Drawing Sheets

WIRELESS COMMUNICATION SYSTEM OF SMART CYCLING EQUIPMENT AND METHOD USING SAME

CROSS-REFERENCE TO RELATED APPLICATION AND CLAIM OF PRIORITY

This application claims priority of a China patent application serial No. 201610873417.8, titled "WIRELESS COMMUNICATION SYSTEM OF SMART CYCLING EQUIPMENT FORMULTI-DEVICES AND METHOD USING SAME" and filed on Sep. 30, 2016, the contents of which are incorporated by reference herein in their entirety for all intended purposes.

TECHNICAL FIELD

The present disclosure relates to communication system and communication method, and more particularly, to a wireless communication system of smart cycling equipment and a method using the system.

BACKGROUND

Nowadays, a wide range of smart cycling equipment is used by a lot of cyclists on riding. In use, a cable is used to connect a smart cycling equipment to a mobile phone, such that sport data can be collected by the mobile phone. In another way, the smart cycling equipment can be connected to the mobile phone by Bluetooth, such that the sport data can be transmitted to the mobile phone without the cable. In this way, the mobile phone receives sport data easily.

However, there are following problems when using technical solutions stated above. Firstly, when a number of smart cycling equipment are connected to the phone via Bluetooth respectively, management of multiple cycling equipment in a single mobile phone simultaneously is necessary, resulting in messy management, inconvenience use, multiple connections, power consumption and other problems. Secondly, Android operating system of the mobile phones is developed by many mobile phone manufacturers, respectively. Versions of the operating system are different from each other. In addition, the mobile phones are integrated with different Bluetooth chips. Accordingly, different Bluetooth chips are coded in different ways. Therefore, many mobile phones fail to connect BLE (Bluetooth low energy) data channels as the BLE data channels are not compatible to the Android operating system. Thirdly, a plurality of steps are necessary when the mobile phone is connected to smart devices (Such as smart helmets), including, for example, scanning BLE data channel, then obtaining headset MAC address (physical address) of the BLE data channel, and further connecting a Bluetooth headset using the obtained MAC address. In summary, it is inconvenience to connecting the smart cycling equipment to the mobile phone in existing technology.

BRIEF DESCRIPTION OF THE DRAWINGS

To illustrate the technical solution according to embodiments of the present disclosure more clearly, drawings to be used in the description of the embodiments are described in brief as follows. Obviously, the drawings in the following description are merely some embodiments of the present disclosure. It is to be noted that for those ordinarily skilled in the art, other drawings can be fetched according to these drawings without doing any creative work.

PREFERRED EMBODIMENTS

The technical solution in the embodiments of the present disclosure will be described clearly and completely accompanying with drawings of embodiments of the present disclosure as follows. Apparently, the described embodiments are only a part of the embodiments of the present disclosure, but not all the embodiments. Based on the embodiments of the present disclosure, all other embodiments achieved by those ordinarily skilled in the art without doing any creative work, should be included in the scope of the present disclosure.

Figure 1:
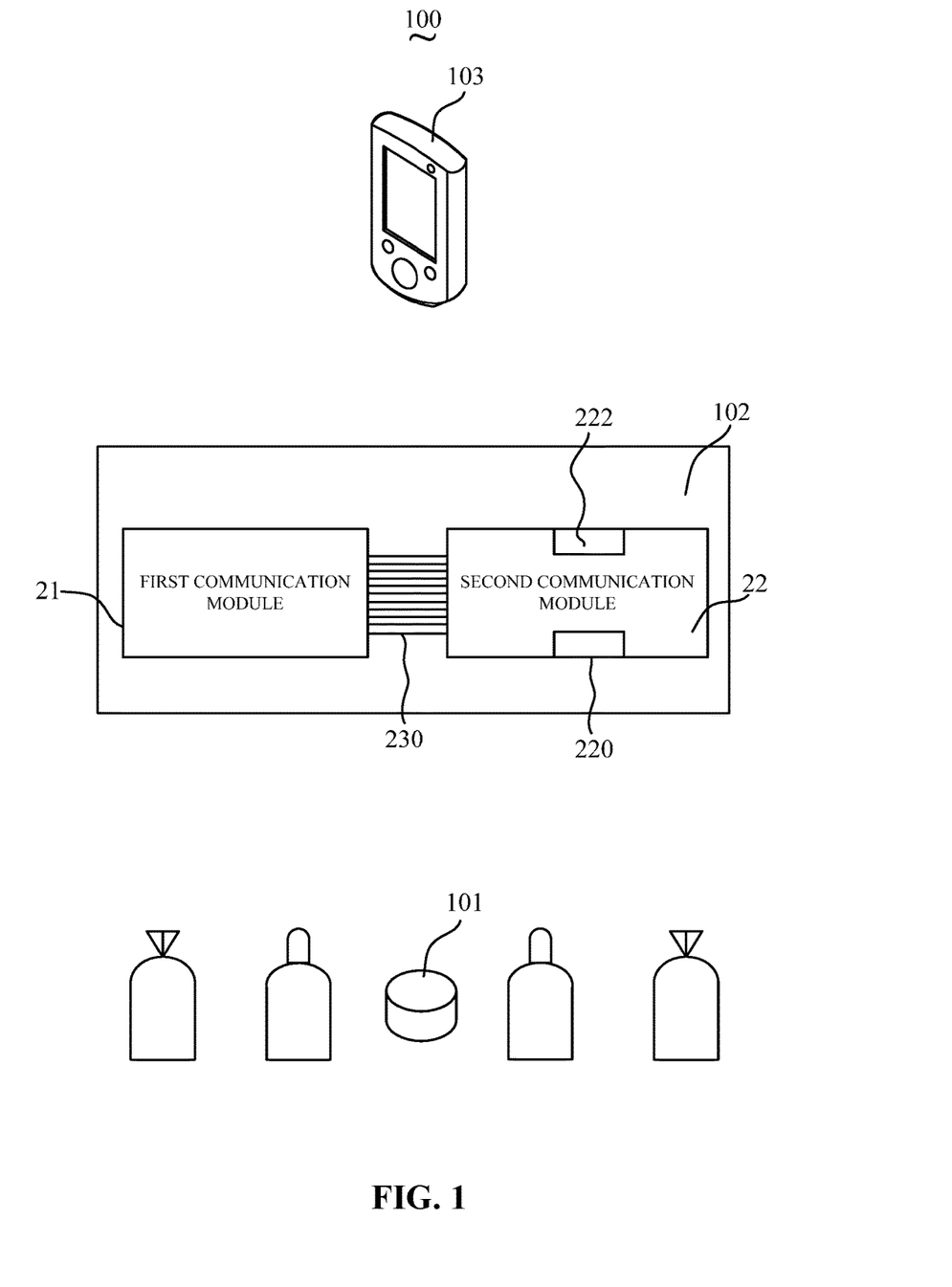
FIG. 1 is a schematic view of a wireless communication system, according to a first embodiment of the present invention.

Referring to FIG. 1, a smart riding multi-device wireless communication system 100 according to a first embodiment of the present disclosure includes a number of peripheral devices 101, a wireless communication device 102, and a terminal 103.

The peripheral devices 101 are used to provide assistant service, such as sensing, controlling, entertainment services, etc., while riding. The peripheral devices 101 may include a sensing device, a displaying device, a Bluetooth headset, or a control device. In this embodiment, the control device may be used to control a component of a cycling equipment (bicycle). For example, the control device may be used to control flickering of a lamp arranged on the bicycle, thus showing a steering direction of the cycling equipment. The peripheral devices 101 can be worn by the bicyclist, or arranged on the bicycle. In one example, the Bluetooth headset may be worn on an ear of the bicyclist, and the Bluetooth headset can be connected to the terminal by the wireless communication device 102. In this way, the Bluetooth headset can be used to answer phone calls and listen to music, etc. In another example, the sensing device can be worn on the cyclist's arm and used to sense physiological parameters of the cyclist. In alternative embodiments, the peripheral devices 101 may include devices such as a sports wristband, a blood glucose meter.

The wireless management apparatus 102 includes a first communication module 21 and a second communication module 22. The first communication module 21 is used to be wirelessly connected to a terminal 103 based on a first communication protocol. The second communication module 22 is used to be wirelessly connected to a terminal 103 based on a second communication protocol. In this embodiment, the second communication module 22 can be used to be wirelessly connected to a terminal 103 based on the second communication protocol.

In this embodiment, the second communication module 22 and the first communication module 21 communicate with each other by a UART (Universal Asynchronous Receiver/Transmitter) 230, or may communicate with each other in other available ways. In this way, a working state of the second communication module 22 and the first communication module 21 can be informed to each other. The working state is used to indicate a connection between the terminal 103 and the first communication module 21 or the second communication module 22. Generally, each of the first communication module 21 and the second communication module 22 includes a Bluetooth chip.

In this embodiment, the second communication module 22 includes a host unit 220 and a device unit 222. It is noted, that the host unit 220 and the device unit 222 each refer to a virtual module in an application layer, which are used to connect the terminal 103 and the peripheral devices 101 in this embodiment.

The terminal 103 can be a portable device such as a mobile phone (smart phone), a tablet computer, etc. based on a first communication protocol or a second communication protocol. The type of communication protocol supported by the terminal 103 depends on a type of the operating system (OS), such as iOS, Android, Microsoft OS or BlackBerry OS, or other possible operating system.

In this embodiment, the first communication protocol supported by the first communication module 21 is Bluetooth SPP (Serial Port Profile) communication protocol, and the second communication protocol supported by the second communication module 22 is BLE (Bluetooth Low Energy) communication protocol. If the terminal 103 is a mobile phone (or other type of terminal) using Android operating system, it is generally compatible with the Bluetooth SPP communication protocol, and thus the terminal 103 establishes a wireless connection with the wireless communication device 102 by the first communication module 21. If the terminal 103 is a mobile phone using the iOS operating system, it is generally compatible with the BLE communication protocol, and the terminal 103 establishes a wireless connection with the wireless communication device 102 by the second communication module 22. As such, connection between the wireless communication device 102 and the terminal 103 can be established, regardless of whether the terminal 103 is an Android operating system (using Bluetooth SPP communication protocol to connect) or the iOS operating system (using BLE communication protocol to connect). It is noted, when the terminal 103 is a mobile phone using the iOS operating system, the terminal 103 is wirelessly connected to the second communication module 22 by the device unit 222.

In this embodiment, the peripheral devices 101 can be connected to the wireless communication device 102 by using BLE communication protocol. Generally, the peripheral devices 101 can be connected to the terminal 103 by the wireless communication device 102. Therefore, multiple connections of several peripheral devices 101 to the terminal 103 are possible, and the peripheral devices 101 can be managed efficiently. In this embodiment, the peripheral devices 101 can be wirelessly connected to the second communication module 22 by the host unit 220.

In alternative embodiment, the wireless communication device 102 may include other communication modules (or chips) based on other wireless communication protocols, such as infrared protocol, Zigbee, etc. In this way, more peripheral devices 101 can be introduced and connected to the terminal 103 by the wireless communication device 102.

In this embodiment, when the wireless communication device 102 establishes a wireless connection with the terminal 103, either the first communication module 21 or the second communication module 22 is connected to the terminal 103, and the other first communication module 21 or the device unit 222 of the second communication module 22 may be informed to turn off (if it is turned on previously) to avoid accidentally connecting to other terminals (not shown) other than the terminal 103, which may resulting misconnection.

Figure 2:
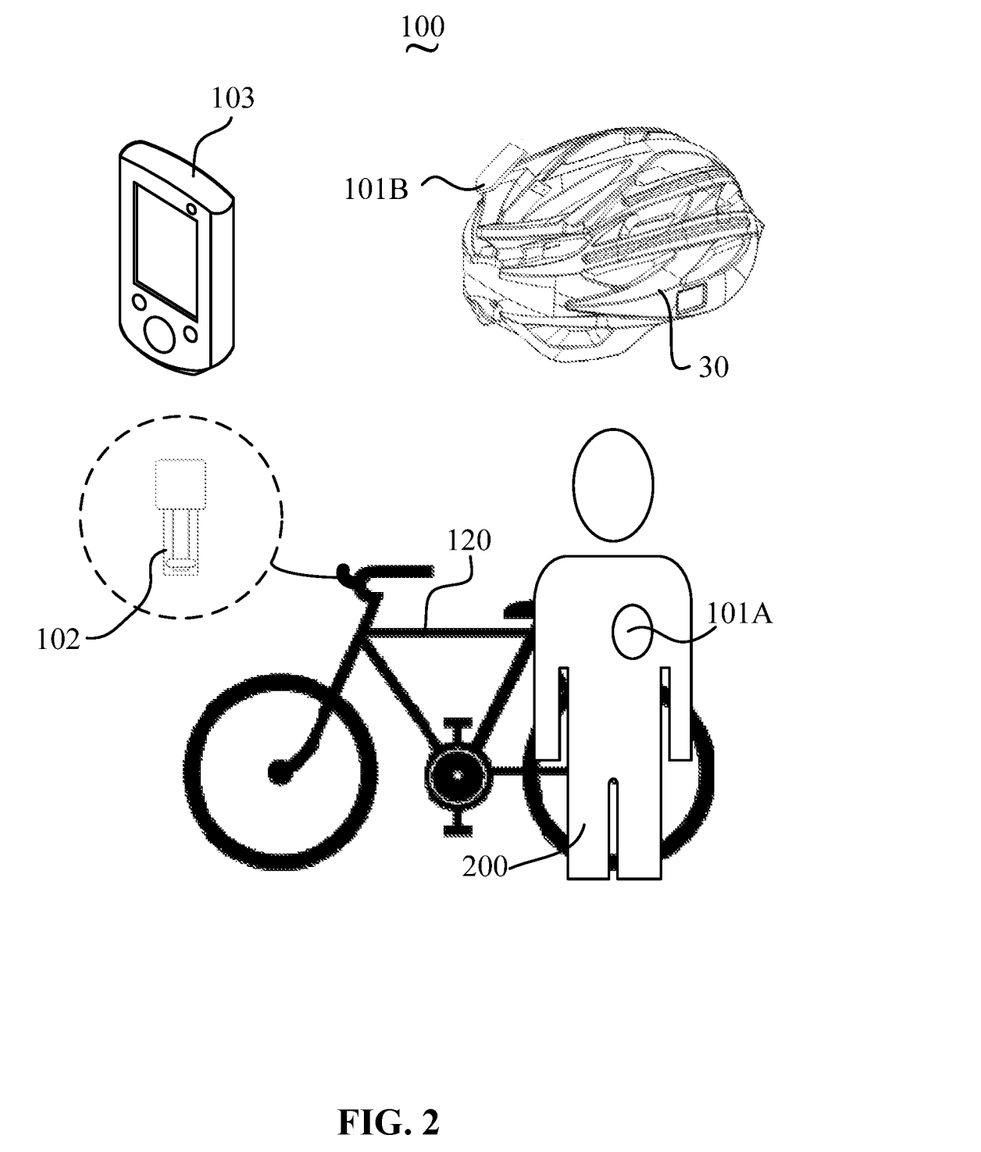
FIG. 2 is a schematic view of the wireless communication system of FIG. 1, showing the wireless communication system is applied by a cyclist.

Referring to FIG. 2, in one application, the communication system 100 may further include a helmet 30 and a cycling device, such as a bicycle 120. And the wireless communication device 102 may be mounted on a bicycle stand of the bicycle 120. In alternative embodiments, the wireless communication device 102 may be mounted on other suitable position of the bicycle 120, such as a bicycle stein.

The helmet 30 can be used to provide head protection for a user (a bicyclist) 200. In use, the peripheral devices 101, such as a Bluetooth headset, may be mounted on the helmet 30. In this embodiment, the peripheral devices 101 may include a heart rate meter 101A and a Bluetooth headset 101B. The heart rate meter 101A is worn by the bicyclist 200, and the Bluetooth headset 101B is mounted on the helmet 30. In addition, the heart rate meter 101A and the Bluetooth headset 101B are wirelessly connected to the second communication module 22 by the host unit 220. In alternative embodiment, the peripheral devices 101 may include devices such as a sports wristband, a blood glucose meter, etc. (not shown). The sports wristband and the blood glucose meter may be worn on the bicyclist's arm for sensing physiological parameters of the bicyclist.

In use, the heart rate meter 101A is configured for measuring real time heart rate, and the measured data is transmitted to the second communication module 22 of the wireless communication device 102. The measured data can be further transmitted to the terminal 103 by the wireless communication device 102 via Bluetooth SPP communication protocol (if the terminal 103 using Android operating system) or BLE communication protocol (if the terminal 103 using iOS operating system).

Figure 3:
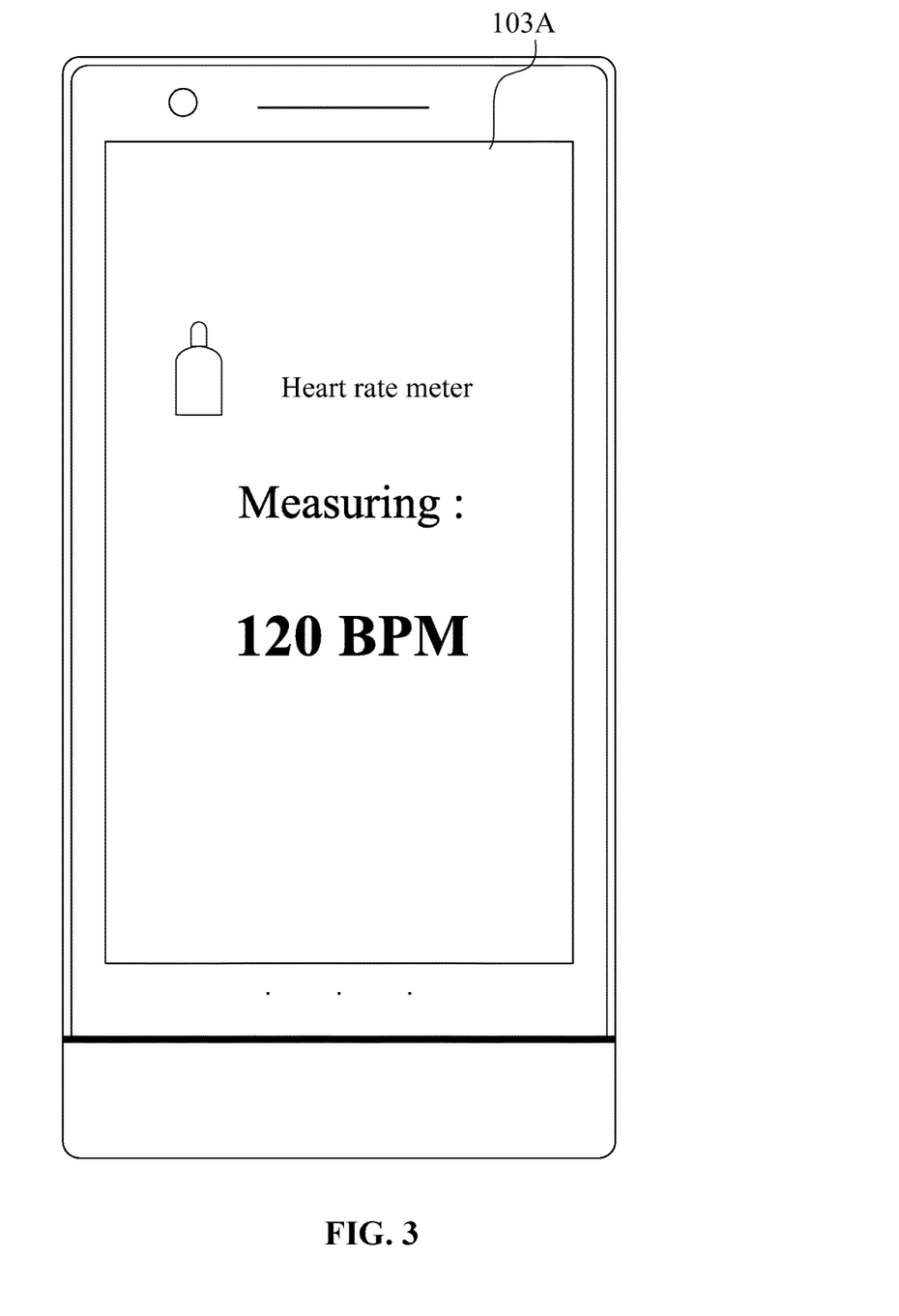
FIG. 3 is a graphic user interface showing measured data from a heart rate meter of FIG. 2.

As shown in FIG. 3, the measured data can be shown by an interface 103A of the terminal 103 (the heart rate shown in FIG. 3 is 120 BPM, which are greater than a normal value). In an application, the measured data may far greater than a normal value. According, a notification information may be generated by the terminal 103 to inform the user 200, i.e., to take a rest. And the notification information can be transmitted to the Bluetooth headset 101B via the wireless communication device 102. On one hand, if the terminal 103 using Android operating system, the notification information is transmitted to the first communication module 21, and further to the second communication module 22 through the UART 230. Then the notification information from the terminal 103 is transmitted to the headset 101B. On the other hand, if the terminal 103 uses iOS operating system, the notification information is transmitted directly to the second communication module 22. Then the notification information from the terminal 103 is transmitted to the headset 101B. Message of the notification information thus can be informed to the user 200 via voice through the Bluetooth headset 101B. The voice for example can be "Please take a rest." It is understood, that the Bluetooth headset 101B can be used to answer phone calls and listen to music, etc.

Figure 4:
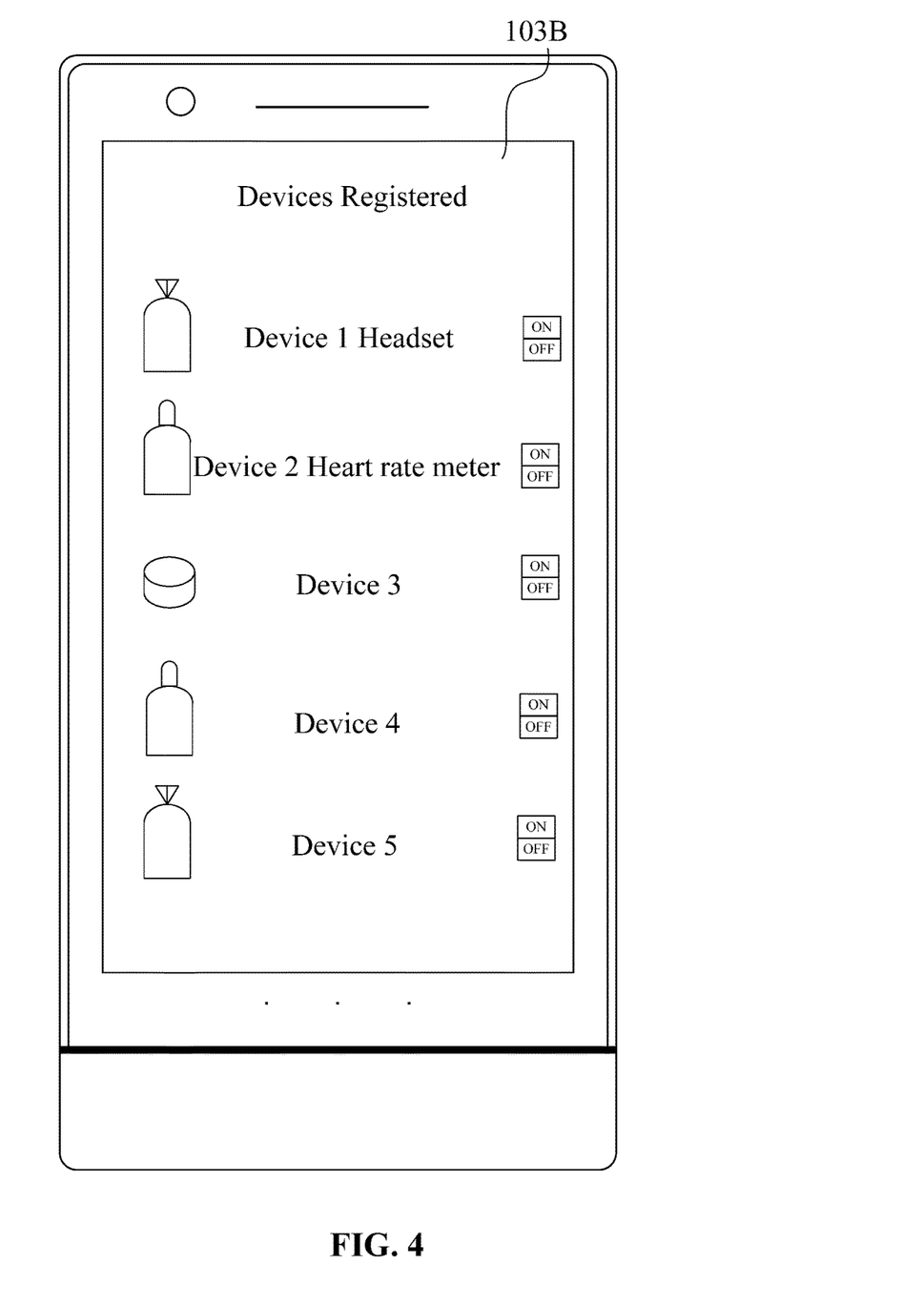
FIG. 4 is a graphic user interface showing a virtual connection relationship between several peripheral devices and the terminal of FIG. 1 are added.

Referring to FIG. 4, once the peripheral devices 101 are wirelessly connected to the terminal 103 via the wireless communication device 102. A virtual connection relationship between the peripheral devices 101 and the terminal 103 can be added to an interface 103B of the terminal 103. The interface 103B is in relation to an application installed in the terminal 103. In one case, if the terminal 103 is an iOS smart phone, the data from the peripheral devices 101 is transmitted to the wireless communication device 102. The data together with a dedicated identification (ID) of the peripheral devices 101 is packaged based on a second communication protocol and transmitted by the second communication module 22 to the terminal 103. A virtual driving module (not shown) of the terminal 103 is used to analyze the packaged data, and further displays the data on the interface 103B. When the user clicks a button on the interface 103B to send a message to the peripheral devices 101, the message together with the dedicated identification is packaged based on the second communication protocol and transmitted to the second communication module 22. The second communication module 22 analyzes the packaged message, and then sends the message to the peripheral devices 101. In this way, an interaction between the peripheral devices 101 and the terminal 103 can be achieved. In another case, if the terminal 103 is an Android smart phone, the data from the peripheral devices 101 is transmitted to the second communication module 22, and further to the first communication module 21 through the UART 230. The data together with a dedicated identification (ID) of the peripheral devices 101 is packaged based on a first communication protocol and transmitted by the first communication module 21 to the terminal 103. A virtual driving module (not shown) of the terminal 103 is used to analyze the packaged data, and further displays the data on the interface 103B. When the user clicks a button on the interface 103B to send a message to the peripheral devices 101, the message together with the dedicated identification is packaged based on the first communication protocol and transmitted to the first communication module 21. The first communication module 21 analyzes the packaged message, and then sends the message to the second communication module 22 through the UART 230. The second communication module 22 sends the message to the peripheral devices 101. In this way, an interaction between the peripheral devices 101 and the terminal 103 also can be achieved.

Referring to FIG. 1, FIG. 2, FIG. 4 and FIG. 5, a smart riding multi-device wireless communication method according to a second embodiment of the present disclosure is shown. The method uses the wireless communication system 100 shown in FIG. 1 and FIG. 2, and includes steps S1 to S4.

Figure 5:
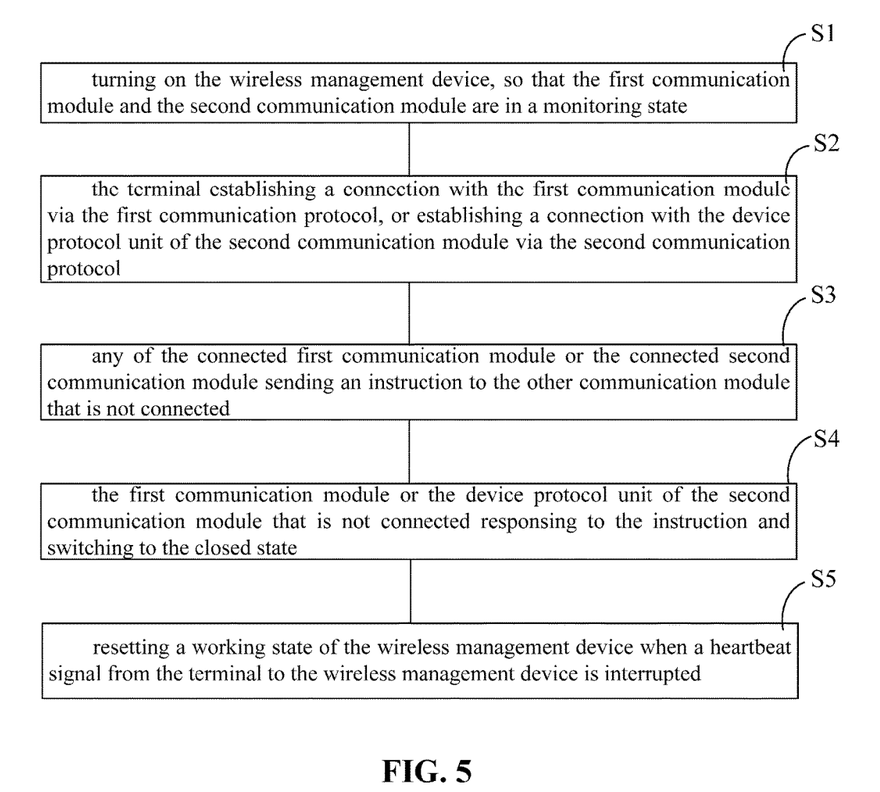
FIG. 5 is a flow chart of a method using the wireless communication system of FIG. 1, according to a second embodiment of the present invention.

Step S1, turning on the wireless communication device 102, so that the first and the second communication modules 21, 22 are in a monitoring state. The first communication module 21 supports a first communication protocol. The second communication module 22 supports a second communication protocol.

In this embodiment, the wireless communication device 102 is turned on by the user 200. When the first and the second communication modules 21, 22 are in the monitoring state, the first and the second communication modules 21, 22 can receive connection request from the terminal 103 or the peripheral devices 101.

In step S2, the terminal 103 establishes a connection with the first communication module 21 via the first communication protocol, or establishes a connection with the second communication module 22 via the second communication protocol.

In this embodiment, when the terminal 103 supports the first communication protocol, the terminal 103 establishes a connection with the first communication module 21. When the terminal 103 supports the second communication protocol, the terminal 103 establishes a connection with the second communication module 22.

As the first communication module 21 supports Bluetooth SPP communication protocol, and the second communication module 22 supports BLE communication protocol. Therefore, if the terminal 103 installs Android operating system (generally based on Bluetooth SPP communication protocol), the terminal 103 is connected to the first communication module 21. If the terminal 103 installs iOS operating system (generally based on BLE communication protocol), the terminal 103 is connected to the second communication module 22.

In this embodiment, the method further includes: the peripheral device establishing a connection with the host unit 220 of the second communication module 22 via the second communication protocol. In this way, a wireless connection between the peripheral device 101 and the terminal 103 can be achieved by the wireless communication device 102.

In step S3, any of the connected first communication module or the connected second communication module 22 sends an instruction to the other communication module (21 or 22) that is not connected.

In application, if the first communication module 21 is connected, the first communication module 21 sends an instruction to the device unit 222 of the second communication module 22. If the device unit 222 of the second communication module 22 is connected, the second communication module 22 sends an instruction to the first communication module 21.

In step S4, the first communication module 21 or the device unit 222 of the second communication module 22 that is not connected receives the instruction and switches to the closed state. In this way, power consumption of the wireless communication device 102 can be reduced.

In this embodiment, when the wireless communication device 102 establishes a wireless connection with the terminal 103, either the first communication module 21 or the second communication module 22 is connected to the terminal 103, and the other first communication module 21 or the device unit 222 of the second communication module 22 may be informed to turn off (if it is turned on previously) to avoid accidentally connecting to other terminals (not shown) other than the terminal 103, which may resulting misconnection.

In this embodiment, when the connection between the first communication module 21 and the terminal 103 or the connection between the second communication module 22 and the terminal 103 interrupts, A working state of the wireless communication device 102 is reset. That is, the method may further include a step S5: resetting a working state of the wireless communication device 102.

In use, when the connection between the first communication module 21 and the terminal 103 or the connection between the second communication module 22 and the terminal 103 interrupts, a heartbeat signal from the terminal 103 to the wireless communication device 102 is interrupted. That is, the wireless communication device 102 cannot receive a heartbeat signal from the terminal 103. And when the wireless communication device 102 cannot receive a heartbeat signal from the terminal 103 for a predetermined time. A working state of the wireless communication device 102 is reset. The first and the second communication modules 21, 22 are again in a monitoring state.

Referring to FIG. 4, once the peripheral devices 101 are wirelessly connected to the terminal 103 via the wireless communication device 102. A virtual connection relationship between the peripheral devices 101 and the terminal 103 can be added to an interface 103B of the terminal 103. The interface 103B is in relation to an application installed in the terminal 103. In one case, if the terminal 103 is an iOS smart phone, the data from the peripheral devices 101 is transmitted to the wireless communication device 102. The data together with a dedicated identification (ID) of the peripheral devices 101 is packaged based on a second communication protocol and transmitted by the second communication module 22 to the terminal 103. A virtual driving module (not shown) of the terminal 103 is used to analyze the packaged data, and further displays the data on the interface 103B. When the user clicks a button on the interface 103B to send a message to the peripheral devices 101, the message together with the dedicated identification is packaged based on the second communication protocol and transmitted to the second communication module 22. The second communication module 22 analyzes the packaged message, and then sends the message to the peripheral devices 101. In this way, an interaction between the peripheral devices 101 and the terminal 103 can be achieved. In another case, if the terminal 103 is an Android smart phone, the data from the peripheral devices 101 is transmitted to the second communication module 22, and further to the first communication module 21 through the UART 230. The data together with a dedicated identification (ID) of the peripheral devices 101 is packaged based on a first communication protocol and transmitted by the first communication module 21 to the terminal 103. A virtual driving module (not shown) of the terminal 103 is used to analyze the packaged data, and further displays the data on the interface 103B. When the user clicks a button on the interface 103B to send a message to the peripheral devices 101, the message together with the dedicated identification is packaged based on the first communication protocol and transmitted to the first communication module 21. The first communication module 21 analyzes the packaged message, and then sends the message to the second communication module 22 through the UART 230. The second communication module 22 sends the message to the peripheral devices 101. In this way, an interaction between the peripheral devices 101 and the terminal 103 also can be achieved.

Overall, the method using the wireless communication system 100 and the wireless communication system 100 in the first embodiment can be used to reduce the management pressure and power consumption of the terminal 103. In the present invention, lower management pressure and power consumption of the terminal 103 is achieved by connecting several peripheral devices simultaneously to a wireless communication device 102, and the terminal 103 is only connected to the wireless communication device 102. In this embodiment, the first communication module 21 and the second communication module 22 are embedded in the wireless communication device 102, thus the wireless communication device 102 can be compatible to the terminal 103 with Android operating system or iOS operating system. In this way, high compatibility of the wireless communication system 100 is achieved.

The contents described above are only preferred embodiments of the present disclosure, but the scope of the present disclosure is not limited to the embodiments. Any ordinarily skilled in the art would make any modifications or replacements to the embodiments in the scope of the present disclosure, and these modifications or replacements should be included in the scope of the present disclosure. Thus, the scope of the present disclosure should be subjected to the claims.

What is claimed is:

1. A wireless communication method, the wireless communication method using a wireless communication system comprising a plurality of peripheral devices, the peripheral devices being configured for providing assistant service; a wireless communication device including a first communication module based on a first communication protocol; and a second communication module based on a second communication protocol, the second communication module including a host unit and a device unit, the host unit being configured for wirelessly connecting to the peripheral devices; and a terminal based on a first communication protocol or a second communication protocol differing from the first communication protocol, wherein the terminal based on the first communication protocol is configured for connecting to the first communication module, and the terminal based on the second communication protocol is configured for connecting to the second communication module via the device unit thereof, the method comprising:

turning on the wireless communication device, so that the first communication module and the second communication module are in a monitoring state;

the terminal establishing a connection with the first communication module via the first communication protocol, or establishing a connection with the device unit of the second communication module via the second communication protocol;

any of the connected first communication module or the connected second communication module sending an instruction to the other communication module that is not connected;

the first communication module or the device unit of the second communication module that is not connected responding to the instruction and switching to the closed state;

the peripheral device establishing a connection with the host unit of the second communication module via the second communication protocol.

2. The wireless communication method of claim 1, further comprising:

adding a virtual connection relationship between the peripheral devices and the terminal to an interface of the terminal.

3. The wireless communication method of claim 1, further comprising:

resetting a working state of the wireless communication device when a heartbeat signal from the terminal to the wireless communication device is interrupted.

4. A wireless communication method, the wireless communication method using a wireless communication system comprising a plurality of peripheral devices, the peripheral devices being configured for providing assistant service; a wireless communication device including a first communication module based on a first communication protocol; and a second communication module based on a second communication protocol, the second communication module including a host unit and a device unit, the host unit being configured for wirelessly connecting to the peripheral devices; and a terminal based on a first communication protocol or a second communication protocol differing from the first communication protocol, wherein the terminal based on the first communication protocol is configured for connecting to the first communication module, and the terminal based on the second communication protocol is configured for connecting to the second communication module via the device unit thereof, the method comprising:

turning on the wireless communication device, so that the first communication module and the second communication module are in a monitoring state;

the terminal establishing a connection with the first communication module via the first communication protocol, or establishing a connection with the device unit of the second communication module via the second communication protocol;

any of the connected first communication module or the connected second communication module sending an instruction to the other communication module that is not connected;
the first communication module or the device unit of the second communication module that is not connected responding to the instruction and switching to the closed state; and
resetting a working state of the wireless communication device when a heartbeat signal from the terminal to the wireless communication device is interrupted.

* * * * *